(12) United States Patent
Omori et al.

(10) Patent No.: US 6,506,946 B1
(45) Date of Patent: Jan. 14, 2003

(54) PROCESS FOR CONTINUOUS PRODUCTION OF ACETYLENEDIOL

(75) Inventors: Hideki Omori, Ichihara (JP); Goro Sawada, Ichihara (JP); Hideo Fukuda, Ichihara (JP); Kazuhiro Imanishi, Ichihara (JP); Tomohiko Sato, Ichihara (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/171,176

(22) Filed: Jun. 12, 2002

(30) Foreign Application Priority Data

Jul. 3, 2001 (JP) .......................................... 2001-201546

(51) Int. Cl.$^7$ .............................................. C07C 33/34
(52) U.S. Cl. ....................... 568/807; 568/813; 568/828; 568/855; 568/874; 568/821
(58) Field of Search ................................ 568/855, 807, 568/813, 828, 874, 821

(56) References Cited

U.S. PATENT DOCUMENTS

| | | | | |
|---|---|---|---|---|
| 4,002,694 A | * | 1/1977 | Hort | |
| 4,117,248 A | * | 9/1978 | Prater | |
| 4,119,790 A | * | 10/1978 | Hort | |
| 5,444,169 A | * | 8/1995 | Wiessner | |

* cited by examiner

*Primary Examiner*—Michael L. Shippen
(74) *Attorney, Agent, or Firm*—Melvin I. Stoltz

(57) ABSTRACT

The present invention provides a process for producing an acetylenediol continuously by reacting a ketone with acetylene in the presence of an alkali catalyst, which process comprises continuously feeding, into a first-stage reactor, a reaction solvent, an alkali catalyst, a ketone and acetylene to give rise to a reaction, continuously introducing the reaction mixture into a second-stage reactor, and continuously feeding a fresh portion of the same ketone into the second-stage reactor to give rise to a reaction.

6 Claims, No Drawings

PROCESS FOR CONTINUOUS PRODUCTION OF ACETYLENEDIOL

BACKGROUND OF THE INVENTION

1. Field of the Invention

The present invention relates to a process for producing an acetylenediol continuously. More particularly, the present invention relates to a process for producing an acetylenediol continuously and efficiently by reacting a ketone with acetylene.

2. Description of the Prior Art

An acetylenediol (hereinafter abbreviated to ADO in some cases) represented by, for example, the general formula (III) or (IV) shown below has been produced generally by reacting 2 moles of a ketone with 1 mole of acetylene in the presence of an alkali catalyst such as potassium hydroxide (see, for example, U.S. Pat. Nos. 2,385,546 and 2,455,058). In this reaction, however, not only ADO is produced but also an acetylenemonool (hereinafter abbreviated to AMO in some cases) which is a reaction product between 1 mole of the ketone and 1 mole of acetylene is formed as a by-product.

Hence, it was attempted to minimize the amount of AMO formed as a by-product and increase the amount of ADO produced. In, for example, JP-A-63-258823, is disclosed a process for producing an alkynediol, wherein a particular ether type solvent and a particular ratio of raw materials are employed to suppress the amount of AMO formed as a by-product.

Meanwhile, in all of the processes for ADO production proposed heretofore, a batch process is employed. As compared with this batch process, a continuous process apparently shows a high production efficiency when a reactor of a given capacity is used. However, the continuous process, as compared with the batch process, is not always advantageous in selectivity of intended product. This is because the production of ADO is a successive reaction via the formation of AMO and, in the case of the continuous process, AMO (an intermediate product) and part of the raw materials introduced are discharged per se and contained in the reaction mixture, reducing the proportion of ADO produced.

SUMMARY OF THE INVENTION

Hence, the object of the invention is to alleviate the above-mentioned drawbacks of the prior art and provide a process for producing ADO by reacting a ketone with acetylene in the presence of an alkali catalyst, which can minimize the amount of the AMO formed as a by-product and increase the proportion of the ADO produced and which can produce the ADO continuously and efficiently.

In order to achieve the above object, the present inventors made a study. As a result, the present inventors found out that by employing a two-stage continuous process which comprises conducting a reaction between a ketone and acetylene in a first reactor, introducing the reaction mixture into a second reactor, and adding a fresh portion of the ketone thereto to give rise to a reaction, ADO can be produced efficiently with the ADO/AMO ratio in the reaction mixture being kept at a high level. The present invention has been completed based on the above finding.

The present invention lies in a process for producing an acetylenediol continuously by reacting a ketone with acetylene in the presence of an alkali catalyst, which process comprises continuously feeding, into a first-stage reactor, a reaction solvent, an alkali catalyst, a ketone and acetylene to give rise to a reaction, continuously introducing the reaction mixture into a second-stage reactor, and continuously feeding a fresh portion of the same ketone into the second-stage reactor to give rise to a reaction.

DETAILED DESCRIPTION OF THE INVENTION

The present invention is described in detail below.

A ketone is used as one of the main raw materials in the continuous ADO production of the present invention. The ketone is an aliphatic or aromatic ketone represented by the following general formula (I)

(I)

(wherein $R^1$ and $R^2$ are each independently an alkyl group, an arylalkyl group, an aryl group or an alkylaryl group each having 1 to 12 carbon atoms), or a cyclic ketone represented by the following general formula (II)

(II)

(wherein $R^3$ is an alkylene group having 5 to 12 carbon atoms).

As specific examples of the ketone represented by the general formula (I), there can be mentioned acetone, methyl ethyl ketone, methyl isobutyl ketone, 2-hexanone, 2-octanone, acetophenone, ethyl phenyl ketone and ethyl tolyl ketone. As specific examples of the ketone represented by the general formula (II), there can be mentioned cyclopentanone, cyclohexanone, methylcyclohexanone and cyclooctanone.

As to the amount of the ketone used, there is no particular restriction. However, the amount is generally 2 to 50% by weight, preferably 5 to 30% by weight based on the reaction solvent (described later) used.

In the present invention, the above ketone is reacted with acetylene in the presence of an alkali catalyst. The alkali catalyst usable herein can be selected from an alkali metal, an alkali metal hydroxide and an alkali metal alkoxide.

Of the above alkali catalysts, as the alkali metal, there can be mentioned, for example, metal sodium and metal potassium; as the alkali metal hydroxide, there can be mentioned, for example, sodium hydroxide, potassium hydroxide, lithium hydroxide, rubidium hydroxide and cesium hydroxide; as the alkali metal alkoxide, there can be mentioned, for example, alkali metal aliphatic alkoxides such as potassium methoxide, potassium ethoxide, potassium isobutoxide, potassium tert-butoxide, sodium methoxide, sodium ethyoxide and the like. There can also be used alkali metal alicyclic alkoxides such as potassium cyclohexyloxide and the like.

The alkali catalyst is used in an amount of 0.1 to 20 moles, preferably 0.5 to 10 moles per mole of the raw material ketone. When the amount of the alkali catalyst is less than 0.1 mole per mole of the ketone, the reaction rate is low and the conversion rate is low. When the amount of the alkali catalyst is more than 20 moles per mole of the ketone, the amount of the alkali catalyst is unnecessarily excessive. Therefore, such amounts are uneconomical.

As to the reaction solvent used in the present invention, there is no particular restriction. As the reaction solvent, there can be used a chain or cyclic aliphatic hydrocarbon, an aromatic hydrocarbon, an aliphatic ether, etc. As the chain aliphatic hydrocarbon, there can be mentioned, for example, saturated hydrocarbons such as hexane, heptane, octane, nonane, decane and the like; and unsaturated hydrocarbons such as diisobutylene, triisobutylene, tetraisobutylene and the like. As the cyclic aliphatic hydrocarbon (alicyclic hydrocarbon), there can be mentioned, for example, cyclohexane, methylcyclohexane, decalin and the like. Further, a mixture of chain aliphatic hydrocarbons, a mixture of cyclic aliphatic hydrocarbons, or a mixture of a chain aliphatic hydrocarbon and a cyclic aliphatic hydrocarbon (a so-called naphthenic solvent) can also be used as the reaction solvent of the present invention.

As the aromatic hydrocarbon among the reaction solvent, there can be mentioned, for example, benzene, toluene, xylene, ethylbenzene, cumene, mesitylene, indene, fluorene and the like. As the aliphatic ether, there can be mentioned, for example, diethyl ether, methyl tert-butyl ether, ethyl tert-butyl ether, diisopropyl ether and the like.

The continuous production of ADO according to the present process is conducted using a two-stage reaction apparatus constituted mainly by two reactors. As the reactors, a tank type is used generally, but a tube type may also be used.

In the flow of the production steps, first, a reaction solvent and an alkali catalyst are fed continuously into a first reactor; then, acetylene and a ketone are continuously fed; in this state, a reaction is allowed to proceed. Part of the reaction mixture formed in the first reactor is continuously withdrawn into a second reactor with the liquid level of the first reactor being kept constant; a fresh portion of the same ketone is continuously fed into the second reactor; and a reaction is further allowed to proceed. Part of the reaction mixture formed in the second reactor is continuously withdrawn at a given rate and treated in a separation and recovery step to recover an ADO (an intended product). Thus, all of the production steps are conducted continuously and thereby a high production efficiency is made possible.

The reaction temperature in the first reactor or the second reactor is 0 to 100° C., preferably 10 to 80° C., and the reaction pressure is ordinarily 0 to 1 MPa (gauge pressure), preferably 0 to 0.2 MPa (gauge pressure) in terms of acetylene partial pressure. A high acetylene partial pressure gives a high reaction rate; however, it is preferred to use a low acetylene partial pressure in order to prevent the decomposition and explosion of gaseous acetylene. Incidentally, in order to prevent the decomposition and explosion, it is possible to dilute acetylene by introducing an inert gas such as nitrogen, argon, propane or the like.

In the above production steps, the molar ratio of acetylene to ketone may be at least 0.6 mole of acetylene relative to mole of the ketone. Generally, the reaction is allowed to proceed in a large excess of acetylene.

The residence time in the reaction system varies depending upon the ratio of raw materials, the temperature of reaction system, the partial pressure of acetylene and other conditions, but is ordinarily 0.5 to 1 hour, preferably 1 to 6 hours.

According to the process of the present invention, there are formed mainly an ADO represented by the following general formula (III) when a ketone of the general formula (I) is used:

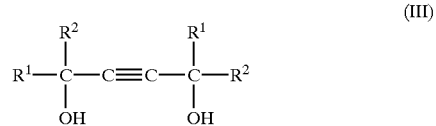

(wherein $R^1$ and $R^2$ have the same definitions as given above), and an ADO represented by the following general formula (IV) when a ketone of the general formula (II) is used:

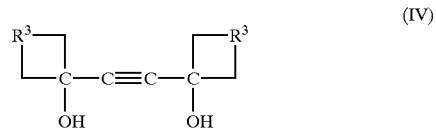

(wherein $R^3$ has the same definition as given above).

The reaction mixture withdrawn from the second reactor is ordinarily subjected first to removal of the alkali catalyst contained therein.

The removal of the alkali catalyst is generally conducted by addition of water to the reaction mixture and extraction of the alkali catalyst therewith. Depending upon the case, it is possible to add an inorganic or organic acid to the organic phase to neutralize and remove a very small amount of the alkali catalyst remaining in the organic phase.

The mixture obtained after the removal treatment of the alkali catalyst contains the reaction solvent, the unreacted ketone, ADO, AMO and a small amount of water used in the removal treatment of the alkali catalyst, is subjected to distillation to remove the unreacted ketone, AMO and a small amount of water, whereby an intended ADO can be obtained.

The ADO obtained by the present invention has a triple bond of high electron density and two hydroxyl groups adjacent thereto. Since these hydroxyl groups synergistically act as highly polar groups, the ADO or its derivative shows strong orientation to metals, antifoaming property, wettability, etc. and are utilized in nonionic surfactants, metal surface-treating agents, medicines, etc.

The present invention is described in more detail below by way of Example. However, the present invention is in no way restricted to the Example.

EXAMPLE 1

Into a first reactor having an internal volume of 10 liters were continuously fed 95 g/hr of a potassium hydroxide powder (purity: 95%) and 800 g/hr of a naphthenic solvent (boiling point range: 210 to 230° C., sp. gr.: 0.79). Acetylene was introduced up to a pressure of 0.02 MPa (gauge pressure). Further, 100 g/hr of methyl isobutyl ketone (a raw material ketone) was introduced. The mixture was allowed to react at a temperature of 25° C. with stirring while the acetylene pressure was kept constant. Then, continuous operation was conducted while part of the reaction mixture being withdrawn so that the residence time became 4.4 hr.

The reaction mixture withdrawn from the first reactor was introduced into a second reactor. Separately, 3.4 g/hr of methyl isobutyl ketone was continuously fed into the second reactor. In this stage, the mixture was further allowed to react. Successively, the mixture in the second reactor was continuously withdrawn so that the residence time became 4.0 hr.

The mixture withdrawn was washed with water and neutralized to remove the catalyst. The resulting material was analyzed by gas chromatography. As a result, the material contained 9.3% by weight of an ADO, i.e. 2,4,7,9-tetramethyl-5-decyne-4,7-diol, 0.5% by weight of an AMO, i.e. 3,5-dimethyl-1-hexyne-3-ol, and 3.6% by weight of unreacted methyl isobutyl ketone.

Comparative Example 1

Into a first reactor having an internal volume of 10 liters were continuously fed 95 g/hr of a potassium hydroxide powder (purity: 95%) and 800 g/hr of a naphthenic solvent (boiling point range: 210 to 230° C., sp. gr.: 0.79). Acetylene was introduced up to a pressure of 0.02 MPa (gauge pressure). Further, 100 g/hr of methyl isobutyl ketone (a raw material ketone) was introduced. The mixture was allowed to react at a temperature of 25° C. with stirring while the acetylene pressure was kept constant. Then, continuous operation was conducted while part of the reaction mixture being withdrawn so that the residence time became 4.4 hr.

The mixture withdrawn was washed with water and neutralized to remove the catalyst. The resulting material was analyzed by gas chromatography. As a result, the material contained 6.1% by weight of an ADO, i.e. 2,4,7,9-tetramethyl-5-decyne-4,7-diol, 4.2% by weight of an AMO, i.e. 3,5-dimethyl-1-hexyne-3-ol, and 2.1% by weight of unreacted methyl isobutyl ketone.

As seen above, the ADO/AMO ratio (molar ratio) in the continuous two-stage process of Example 1 is 10.4 while the ADO/AMO ratio (molar ratio) in the one-stage process of Comparative Example 1 is 1.6. Thus, the ADO/AMO ratio is significantly improved in the process of the present invention.

In the present process for continuous production of the acetylenediol, a continuous two-stage reaction and particular conditions are employed; as a result, the formation of an acetylenemonool (a by-product) can be suppressed, and an acetylenediol can be produced continuously and efficiently with the acetylenediol/acetylenemonool ratio (ado/amo ratio) in the product being kept at a high level.

What is claimed is:

1. A process for producing an acetylenediol continuously by reacting a ketone with acetylene in the presence of an alkali catalyst, which process comprises continuously feeding, into a first-stage reactor, a reaction solvent, an alkali catalyst, a ketone and acetylene to give rise to a reaction, continuously introducing the reaction mixture into a second-stage reactor, and continuously feeding a fresh portion of the same ketone into the second-stage reactor to give rise to a reaction.

2. A process for producing an acetylenediol continuously according to claim 1, wherein the ketone is an aliphatic ketone or an aromatic ketone.

3. A process for producing an acetylenediol continuously according to claim 2, wherein the ketone is acetone, methyl ethyl ketone or methyl isobutyl ketone.

4. A process for producing an acetylenediol continuously according to claim 1, wherein the ketone is a cyclic ketone.

5. A process for producing an acetylenediol continuously according to claim 1, wherein the alkali catalyst is an alkali metal hydroxide.

6. A process for producing an acetylenediol continuously according to claim 1, wherein the reaction solvent is a chain aliphatic hydrocarbon, a cyclic aliphatic hydrocarbon, a mixture of chain aliphatic hydrocarbons, a mixture of cyclic aliphatic hydrocarbons or a mixture of a chain aliphatic hydrocarbon and a cyclic aliphatic hydrocarbon.

* * * * *